United States Patent
Theobald

(10) Patent No.: US 9,463,085 B1
(45) Date of Patent: Oct. 11, 2016

(54) ACTUATOR WITH VARIABLE ATTACHMENT CONNECTOR

(71) Applicant: Daniel Theobald, Sommerville, MA (US)

(72) Inventor: Daniel Theobald, Sommerville, MA (US)

(*) Notice: Subject to any disclaimer, the term of this patent is extended or adjusted under 35 U.S.C. 154(b) by 0 days.

(21) Appl. No.: 13/771,458

(22) Filed: Feb. 20, 2013

(51) Int. Cl.
*A61F 2/08* (2006.01)
*A61F 2/58* (2006.01)

(52) U.S. Cl.
CPC ...................................... *A61F 2/08* (2013.01)

(58) Field of Classification Search
CPC ............. A61F 2/08; A61F 2/58; F15B 13/00
USPC ............ 623/3.12, 14.13, 24, 25, 57; 60/508, 60/325
See application file for complete search history.

(56) References Cited

U.S. PATENT DOCUMENTS

| | | | |
|---|---|---|---|
| 5,040,626 A | 8/1991 | Paynter | |
| 5,080,000 A | 1/1992 | Bubic | |
| 5,351,602 A | 10/1994 | Monroe | |
| 5,529,293 A | 6/1996 | Haugs | |
| 6,168,634 B1 | 1/2001 | Schmitz | |
| 7,104,182 B2 | 9/2006 | Reininger | |
| 7,331,273 B2 | 2/2008 | Kerekes | |
| 7,348,747 B1 | 3/2008 | Theobold et al. | |
| 7,719,222 B2 | 5/2010 | Theobald | |
| 7,837,144 B2 | 11/2010 | Kothera | |
| 2002/0026794 A1* | 3/2002 | Shahinpoor et al. | ........... 60/508 |
| 2002/0157322 A1 | 10/2002 | Pedretti | |
| 2002/0157388 A1 | 10/2002 | Seto | |
| 2007/0084202 A1 | 4/2007 | Hiramatsu et al. | |
| 2009/0173223 A1 | 7/2009 | Kudawara | |
| 2011/0023474 A1 | 2/2011 | Kudawara | |
| 2014/0208937 A1* | 7/2014 | Henry et al. | ...................... 92/90 |

* cited by examiner

*Primary Examiner* — Yashita Sharma

(74) *Attorney, Agent, or Firm* — Albert J. Brunett

(57) ABSTRACT

An apparatus for moving a member has at least one artificial muscle style activation element, and a primary movable connector secured to the at least one artificial muscle style activation element. The primary movable connector is configured to be movable from a first connected location on the member to a second connected location on the member.

10 Claims, 6 Drawing Sheets

| Property | Human Muscle | Hydraulics |
|---|---|---|
| Max. Strain ($L/L_0$) | 30-70% | 10-100% |
| Max. Stress (MPa) | .1-.4 | 20-70 |
| Power Density (W/$m^3$) | $5 \times 10^5$ | $5 \times 10^8$ |
| Density (kg/$m^3$) | 1000-1100 | 1600-2000 |
| Efficiency | 20-25% | 90-98% |
| Activation Frequency ($s^{-1}$) | 5 - 500 | 5 - 300 |
| Control Resolution | $10^{-1}$-$10^{-2}$ | $10^{-5}$-$10^{-4}$ |

ACTUATOR WITH VARIABLE ATTACHMENT CONNECTOR

FIELD OF THE INVENTION

The present invention relates generally to actuators and, in at least one embodiment, to such actuators that are hydraulic or fluid powered and/or used as an artificial or "mechanical" muscle.

BACKGROUND OF THE INVENTION

Actuators typically are mechanical devices that are used for moving or controlling a mechanism, system or the like and typically convert energy into some type of motion. Examples of actuators can be found in any number of applications encountered in everyday life including automotive, aviation, construction, farming, factories, robots, health care and prosthetics, among other areas.

Mobile robotics and advanced prosthetics will likely play important roles in the future of the human race. Actuators frequently are used in these applications that enable movement of a robot or user arm or other appendage or item as desired.

Most existing mobile robots and advanced prosthetics, however, lack the strength and speed necessary to be effective. This is because they suffer from poor specific power (strength×speed/weight) which determines how quickly work can be done compared to another actuator of the same weight.

For example, if such devices are capable of lifting significant weight, they must do so very slowly, which inhibits their adoption for most applications. On the other hand, devices that can move more quickly are just not capable of handling anything more than the smallest weight.

SUMMARY OF THE INVENTION

In accordance with one embodiment of the invention, an apparatus for moving a member has at least one artificial muscle style activation element, and a primary movable connector secured to the at least one artificial muscle style activation element. The primary movable connector is configured to be movable from a first connected location on the member to a second connected location on the member.

In accordance with another embodiment of the invention, a method of changing the movement of a member provides at least one artificial muscle style activation element having a movable connector, secures the movable connector to a first member at a first connected location, and secures the at least one artificial muscle style activation element to a second member. The method then moves the movable connector from the first connected location and, after moving the movable connection, secures the movable connector to a second connected location of the first member.

BRIEF DESCRIPTION OF THE DRAWINGS

The following detailed description will be better understood when read in conjunction with the appended drawings in which there is shown one or more of the multiple embodiments of the present disclosure. It should be understood, however, that the various embodiments of the present disclosure are not limited to the precise arrangements and instrumentalities shown in the drawings.

FIG. 4 is a partial cross-sectional view of one embodiment of the present invention illustrating a plurality of activation elements enclosed in an outer sheath member or the like;

DETAILED DESCRIPTION OF THE INVENTION

Figure 1:
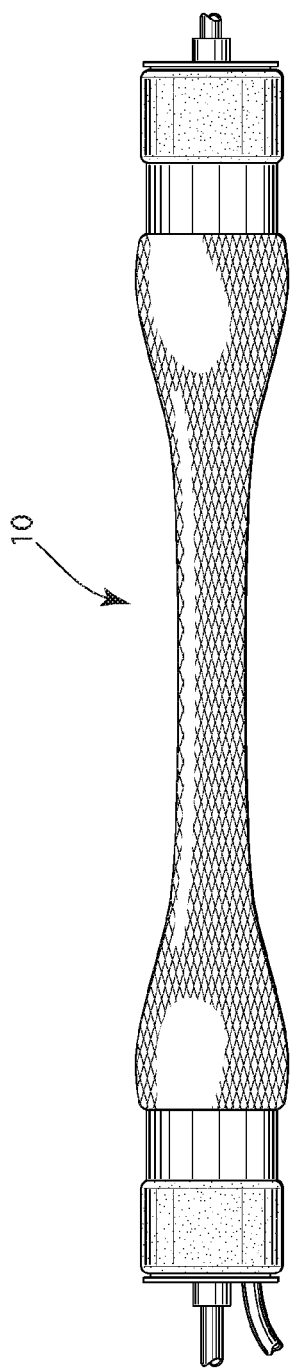
FIG. 1 is a plan view of one embodiment of an activation element of the present invention that may be utilized with the actuator of the present invention illustrated in a first "at rest" position.

Various embodiments of the present invention are described below with reference to the accompanying drawings. It should be understood that the following description is intended to describe exemplary embodiments of the invention, and not to limit the invention.

It is understood that the present invention is not limited to the particular components, analysis techniques, etc. described herein, as these may vary. It is also to be understood that the terminology used herein is used for the purpose of describing particular embodiments only, and is not intended to limit the scope of the present invention. It must be noted that as used herein, the singular forms "a," "an," and "the" include plural reference unless the context clearly dictates otherwise. The invention described herein is intended to describe one or more preferred embodiments for implementing the invention shown and described in the accompanying figures.

Unless defined otherwise, all technical and scientific terms used herein have the same meanings as commonly understood by one of ordinary skill in the art to which this invention belongs. Preferred methods, system components, and materials are described, although any methods and materials similar or equivalent to those described herein can be used in the practice or testing of the present invention.

Many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention. The scope of the present invention is defined by the claims, which includes known equivalents and unforeseeable equivalents at the time of filing of this application Various embodiments of the present invention are directed to various devices that are fluid powered, such as by hydraulics or pneumatics, for example. It is to be understood, however, that some embodiments of the present invention are not limited to these two specific technologies.

In operating a robot, advanced prosthetic, or some other item or mechanism, some type of power system typically is provided to enable particular movement, such as moving an arm or other appendage, for example. As readily can be discerned, in order to provide at least up and down movement to an arm member or the like some type of mechanical or other actuator typically is employed.

In a simple example, a piston driven actuator may be implemented to accomplish this movement. By moving the piston back and forth within a cylinder, the piston rod provides the basic movement to the arm member connected at is distal end.

Another type of actuator can be one that mimics the motion of a real biological muscle in the body of a human or other animal. These artificial or mechanical muscles typically provide some type of expandable member or tube connected at one end to an arm member, such as a forearm of a robot, for example, and at the other end to another member such as the upper arm or shoulder of a robot, for example.

Briefly, in operation, when such a member is expanded in a direction substantially perpendicular to its longitudinal centerline, it essentially contracts the member thereby drawing the arm closer to the shoulder. When the member is thereafter allowed to expand in a direction substantially parallel to its longitudinal centerline, it essentially extends the member and the arm moves away from the shoulder.

One example of such a mechanical muscle is known as a McKibbons style actuator, which is hereby incorporated by reference. It is to be understood, however, that the particular type of mechanical muscle and corresponding expanding member can vary without departing from the teachings of various embodiments of the present invention.

These types of actuators or mechanical muscles exhibit a specific power (strength×speed/weight) that far exceeds that of existing actuators typically used in robots that suffer from poor efficiency, noisy operation, high cost and maintenance challenges, among other drawbacks. These drawbacks and more are readily solved by the design of illustrative embodiments of the present invention that readily exceed the performance of real biological muscles.

Additionally, as the human race begins to work in close collaboration with robots, advanced prosthetics, and similar machines and mechanisms, they are anticipated to expect the robots to be stronger, faster, have better endurance, be more precise, and cost less than other options. They also may expect robots to quickly and efficiently carry out their assigned physical tasks with little or no down time for maintenance or fatigue, for example.

Biological muscles consist of many smaller "actuator" fibers called sarcomeres, bundled in parallel. During movement of a body limb, for example, all or just a partial subset of available fibers may be activated depending on the task involved.

By scaling down the size of mechanical muscles, arranging them in bundles and designing them to handle much higher hydraulic pressures, a large increase in specific power is achieved. Significant reduction in the overall weight of this design, among other factors, leads to this increase in specific power. At the same time, by activating any number of the actuators arranged in such a bundle to vary the power output for the task at hand, significant power savings is achieved.

When employing these types of mechanical or artificial muscles, the trend is to provide a single actuator for each direction of desired motion. With this design, variations in movement and control are limited.

One key feature among many of illustrative embodiments is to provide a plurality of discrete, readily interchangeable mechanical muscles for each direction of desired motion, where each muscle has a predetermine power capability. This concept dramatically teaches away from conventional thinking, provides a number of distinct and unexpected results and advantages in the art, and essentially revolutionizes the potential applications possible.

As one example, by using a plurality or bundle of muscles, the number of muscles activated can vary depending on the power requirements of the task at hand. One advantage of this novel design concept is power conservation, which is particularly important with mobile robots as well with overall environmental concerns.

Another advantage is in the type and number of potential applications that become available by using a bundle of muscles. With conventional thinking being to merely increase the size of the actuator or muscle to increase the power capability of the device, applications are limited to larger and larger devices. In the design discussed herein, smaller and smaller applications are possible since the actuators can be smaller and lighter, among other attributes.

Examples of various hydraulic systems and robotic applications where a mechanical muscle may be employed can be found, for example, in applicant's issued U.S. Pat. No. 7,348,747 filed Mar. 30, 2006, issued U.S. Pat. No. 7,719, 222 filed Mar. 24, 2008 and pending U.S. patent application Ser. No. 12/731,270 entitled "Task Flexibility for Actuators" filed Mar. 25, 2010 and related co-pending applications, all of the disclosures of which are hereby incorporated by reference. It is to be understood, however, that the particular details of the hydraulic system itself, as well as the robot, vehicle, tool, heavy equipment, actuator, or other apparatus, can vary without departing from the teachings of various embodiments of the invention.

Figure 2:
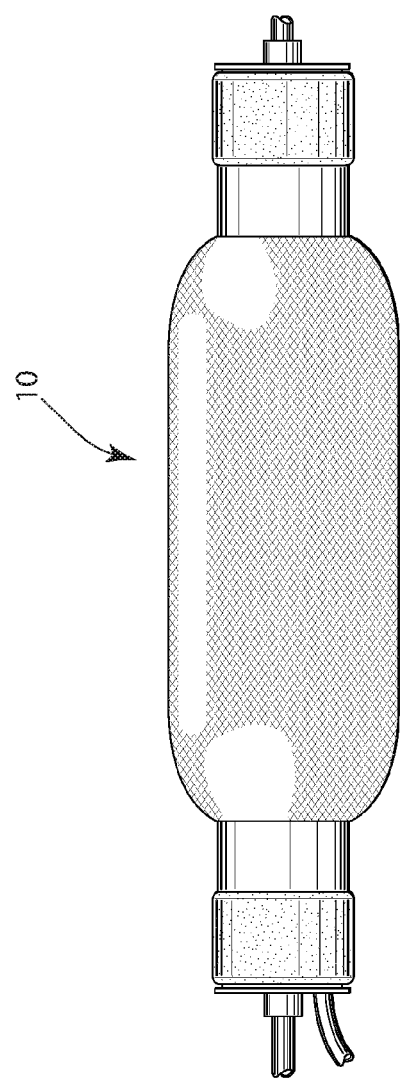
FIG. 2 is a plan view of the element of FIG. 1 illustrated in a second activated position.

FIGS. 1 and 2 generally illustrate one embodiment of a mechanical muscle 10 that may be employed in various embodiments of the present invention. The muscle 10 also is referred to as an "activation element 10, "artificial muscle style activation element," or as an "actuator 10." The particular size, shape, material and design of the muscle 10 can vary so long as it falls within the scope of the appended claims.

Briefly, in operation, FIG. 1 generally illustrates the muscle 10 in an extended or at-rest position where no fluid is provided to the interior of the muscle 10. As FIG. 2 generally illustrates, when fluid is provided to the interior of the muscle 10, the muscle 10 expands in a direction substantially perpendicular to its longitudinal centerline, essentially contracting the muscle 10, thereby shortening it length. Conversely, when fluid is essentially released from the interior of the muscle 10, the muscle 10 expands in a direction substantially parallel to its longitudinal centerline, thereby increasing its length.

As readily can be discerned and described in more detail below, if the muscle 10 is attached on opposite ends to other members, desired movement between the members can be achieved. Additionally, the particular type, shape, material and design of the muscle 10 can be varied to in turn vary the movement between the two members to which it is attached.

Figure 3:
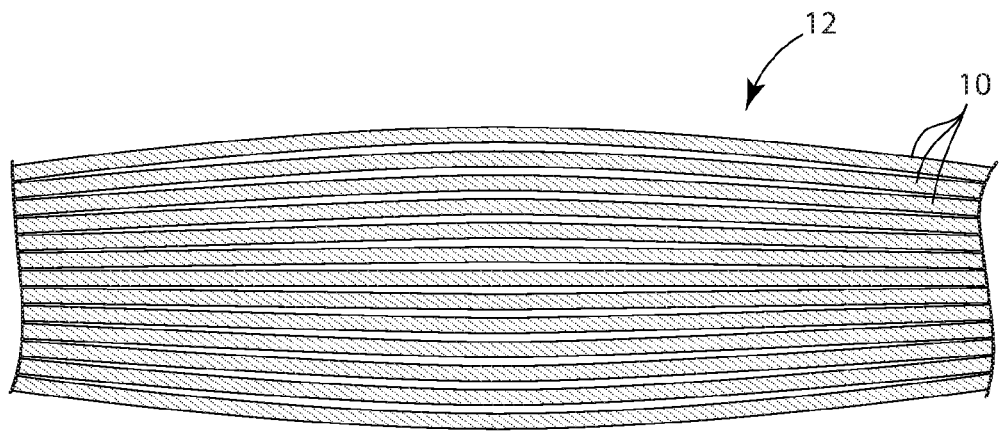
FIG. 3 is a partial plan view of one embodiment of the present invention illustrating a plurality of activation elements arranged in a bundle.
Figure 4:
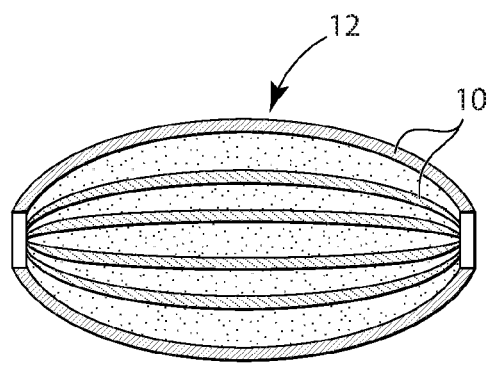
Figure 5:
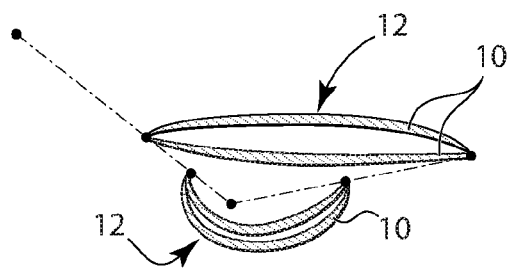
FIG. 5 is a semi-schematic view of one embodiment of the present invention illustrating one potential use of the activation elements.

As FIG. 3 generally illustrates, the number of muscles 10 utilized can be expanded to vary the performance of the muscle 10 as needed. In particular, by providing a number of muscles 10 in one or more bundles 12 a corresponding increase in the lifting or movement capacity of the muscle 10 or bundle 12 can be accomplished.

Existing actuators for robot, prosthetics, and the like are heavy and lack the specific power necessary for effective designs. This limits the number, strength, and speed of each degree of freedom in a robot or the like.

While the human body has over 600 individual skeletal muscles, the most advanced humanoid robots in existence today can afford only 50 or so conventional actuators and still end up weighing twice as much as a human, which can present a safety issue when working closely with humans. To be truly capable and safe, robots and prosthetics need to be stronger, weigh less, and have many more degrees of freedom than current systems.

Pneumatic actuators or mechanical muscles are limited by their relatively low operating pressure of about 100 PSI and poor controllability due to the compressible nature of air, which is generally the working fluid in such pneumatic systems. By utilizing a design incorporating hydraulically actuated actuators or mechanical muscles as described herein that are capable of operating at much higher pressures of about 3000 PSI, incredible increases in power are provided while increasing controllability.

As the goal of robotics aims to supplant human labor, human skeletal muscle is an appropriate standard to beat. Muscles provide adaptive, integrated closed-loop positional control; energy absorption and storage; and elastic strain to allow for deformation of tissue under loads. They are rapidly responsive and able to adjust spring and damping functions for stiffness and compliance in stability, braking, and more. A viable artificial actuation approach should at least provide such comprehensive functionality; additionally such an approach should meet or exceed the set of performance metrics of human muscles and improve upon muscles' limited peak performance envelope.

Figures 6, 7:
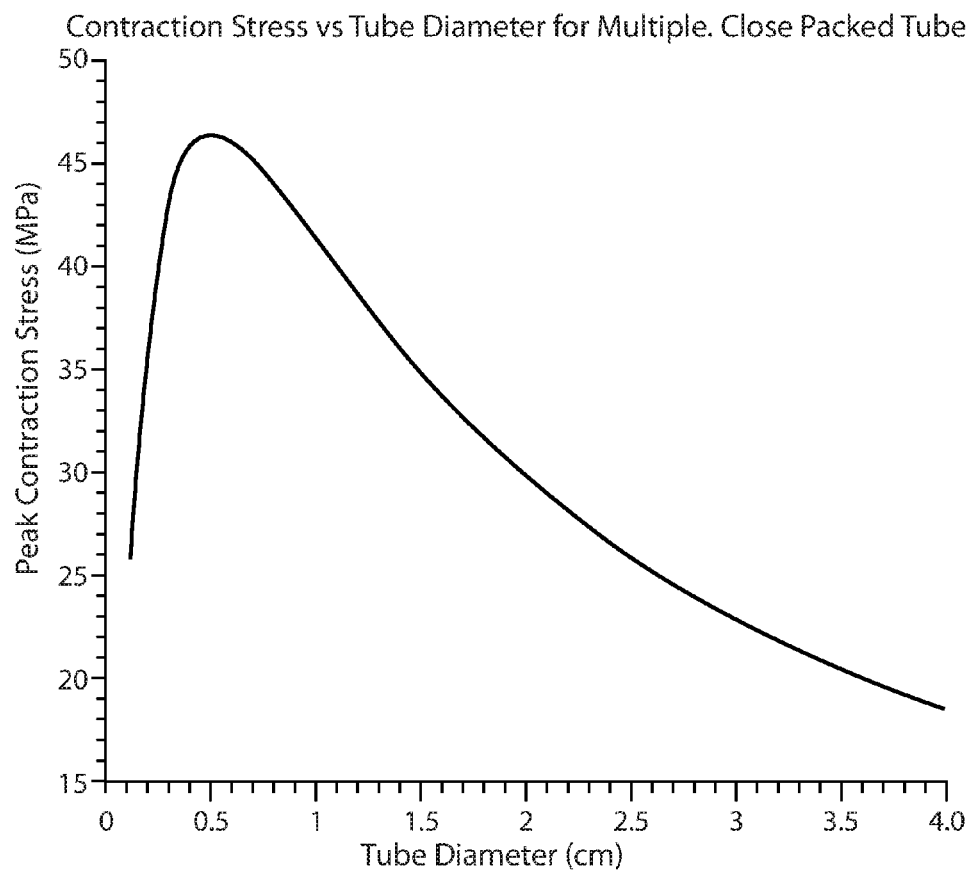
FIG. 6 is a table illustrating performance characteristics of human muscles and hydraulic systems.
FIG. 7 is a graph illustrating contraction stress vs. tube diameter.

As FIG. 6 illustrates, hydraulic mechanical muscles 10 outperform human muscle in power density, efficiency, stress vs. strain, frequency, control resolution, and will closely match human muscle in density, and variable compliance ability. In addition, hydraulic mechanical muscles will also achieve significant improvements in the state of the art in terms of cost, manufacturability, flexibility in application, and scalability. As described earlier, the power density factor is an important criterion that implies the simultaneous speed and strength needed for things like running and throwing.

While existing somewhat exotic actuator technologies may exceed any single actuator performance metric, they are unable to provide comparable overall performance. For example, piezoelectrics are unacceptably brittle; shape memory alloys (SMAs) have prohibitively slow response cycles due to a temperature-dependent actuation; magnetostrictors require constant, fragile magnetic fields at large scales.

Additionally, electroactive polymers (EAPs), require large and potentially unsafe actuation voltages (>1 kV, typical) and consistent current to maintain displacement, possibly making them unacceptably inefficient while chemically-activated ionic versions do not consistently sustain DC-induced displacement and have slow response times. Additionally, EAPs have difficulty damping for low frequency vibration and inaccurate position sensing capabilities due to inherent actuator flexibility. Since biological joints are analogous to direct-drive actuation and therefore largely backdrivable (i.e. resilient), the same forces acting upon an EAP actuator in a leg for example will cause it to deform and perform unexpectedly. Most of all, these materials are prohibitively expensive and complicated to manufacture.

More conventional existing actuators fail to replicate muscle-like performance for a number of reasons. Electromagnetic approaches lack any real scalability because of their need for expensive, high power, rare-earth magnets. Their highly specialized motor design precludes the force output properties of muscle tissue.

Out of all available actuation techniques, pneumatic actuators, particularly of the "mechanical muscle" or McKibbens type described above appear to most closely match the force-velocity and force-length characteristics of human muscle. These pneumatic actuators exploit the high power density, light weight, and simplicity of fluid power, but precise control of these systems is difficult because of the compressibility of air and the inherent excessive compliance, hysteresis, nonlinearity, and insufficient contraction rates of rubber actuators.

In contrast, a hydraulic approach to mechanical muscle fluid power avoids these limitations while at the same time offering inherent advantages for adjustable compliance, proportional force output, energy recovery and efficiency, precise control, and scalability. This broad complement of properties makes hydraulics an excellent candidate for biometric actuation.

In fact, the overall superior performance of hydraulics for vibration damping, actuation frequency, and volumetric power for compact designs in general applications are well known. Furthermore, since hydraulics operate on virtually the same principles as pneumatics, which perform comparably to natural muscle, they are similarly suitable for artificial muscles if used in the right actuator design. As such, a new paradigm in actuator approach is provided in at least one embodiment of the present invention that leverages the superior power and controllability of hydraulics with biophysical principles of movement.

One of the many significant benefits of a bundle of mechanical muscles approach is that simultaneous activation of all of the bundled actuators becomes unnecessary; rather, there is the potential to activate only the minimum of muscle fibers or actuators that are needed for the task. Benchtop tests demonstrated a 3 inch displacement for a strain of 70%. Maximum pulling force (before material failure) was approximately 95 pounds at a pressure of nearly 1800 PSI. This bundle approach to mechanical muscles will achieve at least 10 times the specific power of human muscle while achieving similar impedance control, and will be practical for use in robotic systems. As this type of system is perfected, additional increases in specific power are anticipated.

Human muscle is comprised of both pennate (fibers aligned at an angle to the muscle's long axis) and parallel-fibred muscles, each with functionally-specific mechanical features: pennate muscles act around joints, rotating their angle to act as variable gears, while parallel-fibered muscles are the workhorses (cf. biceps brachii or soleus) of load-bearing movement. The mechanical advantage of a bundle of small or miniature McKibbons type actuators is similar: since Pascal's Law holds that increases in fluid pressure are distributed equally to all parts of a system, force increases proportionally with the cross-sectional area of the actuator.

Since it has been identified that adjustable force output can be a function of increased actuator diameter, using bundles or clusters of miniature McKibbons type actuators can scale upward in cross-sectional area through the addition of more actuators; since the individual actuator size does not increase, tolerances for pressure and stress remain the same while force output increases.

In a cylindrical pressure vessel, like a McKibbons Actuator, the effect of hoop stress from fluid pressure dominates the tensile stress in the individual fibers. It is established that $$T = \frac{PDd}{2\sin(\theta)} \quad (1)$$

where P, D, d, and θ are the fluid pressure, actuator tube inner diameter, fiber diameter, and weave angle respectively. As expected, the hoop stress, and therefore the tension, increase as a function of actuator diameter. The relationship for the peak contractile force (F) of a McKibbons style actuator can be expressed as:

$$F = \frac{\pi}{4} D_o^2 P \frac{1}{\sin^2(\theta)} (3\cos^2(\theta_0) - 1) \quad (2)$$

where θo and Do represent the weave angle and diameter of the actuator while at rest. For a given fiber, with diameter d and max tensile stress $\sigma_t$, and initial weave angle θo we can use Eqns. (1) and (2) to determine the maximum allowable fluid pressure as a function of diameter Do.

$$T_{max} = \frac{\pi}{4} \sigma_t d^2 \quad (3)$$

$$P_{max} = T_{max} \frac{\sin(\theta_o)}{2Dd} \quad (4)$$

Substituting $P_m$ax into (2) allows for calculation of the peak contractile force $F_{max}$ as a function of diameter. Here, we consider the bundle of McKibbons actuator or BoMA approach where a single, large actuator can be replaced with multiple smaller actuators. By using smaller cylinders, a significantly higher fluid pressure can be used. Let t be the thickness of the actuator tube and fibers, so that the outer diameter of the actuator is D+t. Then, we can calculate the peak contractile stress as, $$\sigma_{max} = \frac{4F_{max}}{\pi(D+t)^2} \quad (5)$$

Using sample system parameters for θ, d, and t, and the tensile strength for high strength polyethylene, FIG. 7 shows the peak contraction stress over a range of possible tube diameters. Note the peak near D=0.6 cm, which illustrates that the tube diameter at which the greatest force density can be achieved. In a real system, cylinders can only be close packed to overall density of 78%, so there is a slight advantage to using a single McKibbons actuator. However, as seen in the figure, this 22% difference is small when compared with the improvement in force density from using multiple cylinders. When compared with a single actuator with a 4 cm diameter, the BoMA approach with multiple 0.6 cm diameter actuators more than doubles the potential force density.

Hydraulics also enables important advantages for replicating the principle of co-contraction in biarticulate, flexor/extensor muscle groups. Co-contraction has been shown to perform multiple functions in humans and animals, including a reduction of variability in reaching movements through increased stiffness produced by muscle activation and robustness to perturbations and an increase in joint impedance for greater limb stability, the quick generation of torque, and compensation for torque components orthogonal to desired trajectories.

In the BoMA approach, the stiffness inherent to the incompressible hydraulic fluid allows for precise control of a manipulator or leg through co-activation; for example, differences in simultaneous agonist (biceps brachii) contraction and antagonist (triceps brachii) contraction determine the position of the forearm. Isometric force can be determined by summing antagonist muscle torques; stiffness and torque can thus be controlled independently. This stiffness can be dynamically increased or decreased according to task requirements; greater stiffness allows for more precise control, while decreased stiffness enables more compliance. Additionally, the parallel elastic element in musculature acts as a lightly damped, non-linear spring which is the primary source for the passive tension (i.e., compliance) under eccentric loads which facilitates the contractile element's return to resting length. The elastic sheath of the fibers will provide some of this passive tension.

Hydraulics will inherently provide the remainder of damping using valves with adjustable orifices to produce a damping force proportional to the speed of movement. Since the biological tendon may contribute a great portion of compliance and therefore affect stiffness during locomotion, elasticity should be adjustable. Such stiffness will need to be counterbalanced with sufficiently high-bandwidth active and passive compliance to provide robustness to collisions and to maximize safety around humans. Thus, a key design characteristic of the BoMA approach is a range of compliance in both spring and damping characteristics. Approaches to compliance can be divided into two categories: passive and active. Passive approaches use the natural characteristics of materials to achieve spring and damping effects. Active compliance, on the other hand, is achieved by moving the actuator in a way that mimics a desired compliance.

Previously developed active approaches, such as the Series-Elastic Actuator use an actuator and tight control loop to mimic compliance of passive materials. In this approach, basic compliance is achieved through placement of spring between actuator and load; a linear potentiometer used to measure the spring's length provides force sensing that is combined with position sensors to facilitate rapid adjustments for desired position, velocity, springiness and damping gains. The series-elastic principle can be implemented using a hydraulic actuator that features low impedance and backdriveability; accordingly, the BoMA approach will be backdriveable.

For the BoMA approach, passive compliance is achieved through a number of means, including: the natural elasticity of the contractile sheath of the BoMA fibers, which provides a small restoring force back to resting length; through the elastic "tendons" arranged in series with the BoMA clusters, connecting them, with connectors at various locations (e.g., at the ends of the clusters), to the robot skeleton; through co-contraction control policies using adjustable stiffness;

and through scalable actuation of individual fibers within clusters, exploiting the compliance of the surrounding unpressurized actuator material.

The inventors discovered that the point of connection of the actuator 10 or bundle 12 with its underlying structure can have a significant impact on device performance. For example, when designing a robot, the system designer can select an optimal location for the bundle connection to a synthetic bone to maximize the torque, sensitivity, and speed (among other things) of that portion of the robot. Those skilled in the art therefore often make many assumptions and complex calculations to ensure that this connection is that the most optimal location/spot.

Sometimes, however, there is no single optimal location for making that connection (referred to as a "connection location"). For example, a robot may require a specific performance in a first circumstance that has a first optimal connection location, and a different specific performance in a second circumstance that has a second, different connection location. In fact, a single robot can have more than two optimal connection locations for one or both ends of a single muscle 10, further complicating the overall design.

Figure 8A:
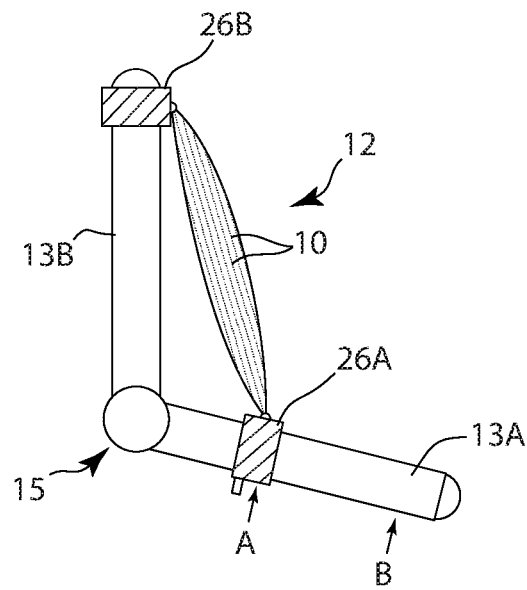
FIG. 8A schematically shows a bundle of actuators with its movable connector connected in a first location of a member.
Figure 8B:
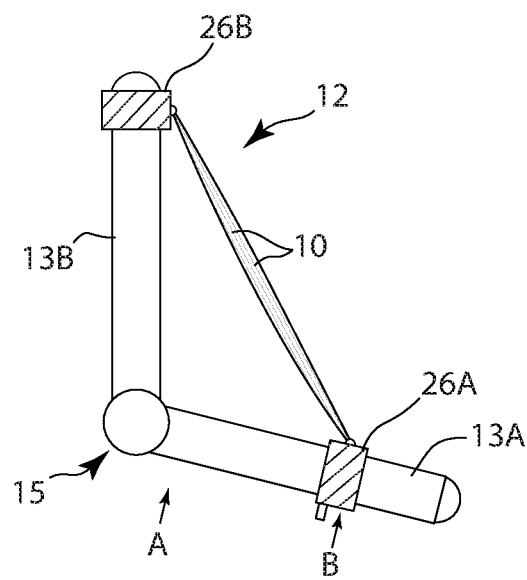
FIG. 8B schematically shows a bundle of actuators with its movable connector connected in a second location of the same member of FIG. 8A.

After considering these issues, the inventors realized that a movable connection could provide the benefits for many different performance requirements without requiring the noted design trade-offs. To that end, FIG. 8A schematically shows a bundle 12 having one end with a movable connector 26A fixedly secured/connected with a first member 13A at a first spot—location A. In contrast, FIG. 8B schematically shows the same movable connector 26A and first member 13A, but with the movable connector 26A fixedly secured/connected to a different spot—location B.

More specifically, like other embodiments described above, the bundle 12 in FIGS. 8A and 8B has a plurality of activation elements 10 with connectors at both ends; namely, the noted first connector 26A (noted above) and a second connector 26B. The first connector 26A, which, as noted above is a movable connector, statically/fixedly connects with the first member 13A, while the second connector 26B is not movable and statically/fixedly connects with a second member 13B. In the example shown in FIGS. 8A and 8B, the noted two members 13A and 13B are rotatably and movably connected at a joint/hinge 15. Accordingly, the two members 13A and 13B move/rotate relative to each other about their common connection.

Of course, a hinge 15 is but one of a plurality of different types of movable connections between the two members 13A and 13B. For example, the connections can be a telescoping connection, where the bundle 12 moves one of the members 13A or 13B in a direction that is generally parallel to the longitudinal axis of the other member 13A or 13B. As another example, one member 13A or 13B may move relative to the other in a linear direction where the respective longitudinal axes are not parallel.

The two members 13A and 13B and bundle 12 can be part of a larger structure, such as, among other things, a robot, prosthetic leg or arm, mechanized device, dynamic guy wire, self-stiffening device, tourniquet, prosthesis attachment device, body worn apparatus, or other mechanism. The members 13A and 13B can be formed from a variety of materials such as metal, plastic, carbon fiber or any other material so long as they function as described herein. Accordingly, discussion of various embodiments in terms of a robot is for illustrative purposes only and not intended to limit all embodiments.

When secured to the first member 13A and used in an anticipated manner, the movable connector 26A should have a secure and static/fixed connection to its designated connection location. For example, when used in the configuration of FIG. 8A, the movable connector 26A should be static during use at a first mode designated as location A. Then, at some other time, the movable connector 26A may be moved to a second mode designated as location B where it also forms a static connection until it is subsequently moved along the first member 13A to another connection location.

As noted above, in the embodiment of FIGS. 8A and 8B, the second connector 26B is not movable along its member 13B and thus, is not considered to be a "movable member." If one were to attempt to move the second connector 26B along the second member 13B, then that person necessarily would have to take some unusual and unintended actions, such as forcibly removing the connector 26B from its connection with the second member 13B. For example, that person may physically cut the connector 26B and reform it at another location. Because it is not necessarily designed to be moved, one attempting to move it in this or some other similarly forcible manner could damage the connector 26B. This is in contrast to the movable connector 26A, which is designed to be moved along the first member 13A in a repeatable manner without damage. There is no need to cut, weld, or take unusual or destructive steps to force it to be moved from one point to another point along the first member 13A.

Figure 9:
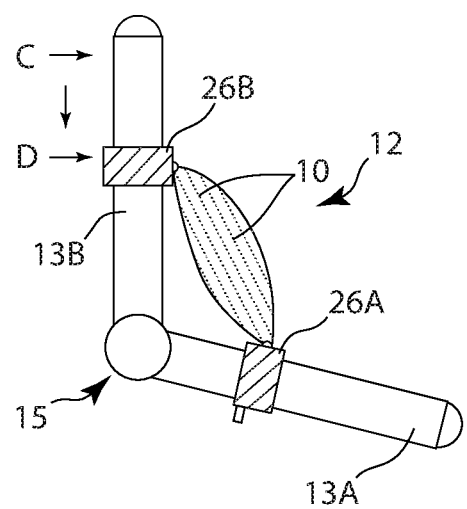
FIG. 9 schematically shows a bundle of actuators with two movable connectors.

Some implementations can benefit from having both connectors 26A and 26B being movable along their respective members 13A and 13B. FIG. 9 schematically shows one implementation of such a design, in which both the first and second connectors 26A and 26B are "movable connectors." More specifically, FIG. 9A shows one example in which the second connector 26B was moved along the second member 13B from connection location C to connection location D.

Figure 10:
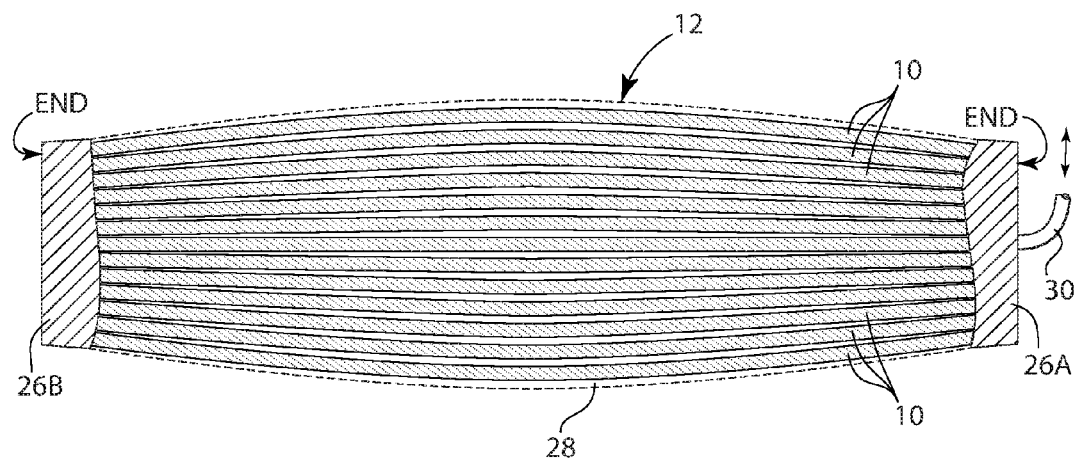
FIG. 10 schematically shows more details of a bundle of actuators in accordance with one embodiment of the invention.

FIG. 10 schematically shows more details of one embodiment of the bundle 12 shown in FIGS. 8A, 8B, and 9. This figure shows the bundle 12, with its plurality of independent activation elements 10 that each can be independently activated and controlled as needed to vary its output power. Accordingly, as discussed above, only selected numbers of activation elements 10 may be actuated, depending upon the requirements of the application. For example, only one or two activation elements 10 may be actuated, or all of the activation elements 10 may be actuated. The ultimate use or function is expected to determine the number of activation elements 10 that are actuated. Among other ways, the specific activation elements 10 that are actuated can be selected automatically by some prescribed logic, on the fly by some prescribed logic, or in a manner selected by a user at the moment of use This figure also shows one embodiment of the first and second connectors 26A and 26B, one or both of which may both be movable. Those connectors 26A and 26B may be implemented from a wide variety of connection mechanisms that are adapted to be removably connectible with some underlying structure, such as one of the members 13A or 13B. For example, among other things, the connection mechanisms may include Velcro, snaps, buttons, or other securing mechanisms known in the art that provide a removable connection.

Some removable connection mechanisms alternatively or also may include a ring or similar frame-like structure (e.g., shown schematically in FIGS. 8A-9) that circumscribes the member 13A or 13B to which it is secured. Spring loaded bolts extending through the frame of the ring may removably lock the connector 26A or 26B to corresponding apertures through specified parts of the underling member 13A or 13B. To move the connector 26A or 26B, manual or automatic mechanisms may retract the bolt and slide the sleeve to the next connection location. The bold then snaps back into the aperture at that spot to lock the sleeve to its new connection location. Of course other connection mechanisms may be used and those discussed above merely are exemplary of various embodiments.

Some of the above noted connection mechanisms may be modified to eliminate their movability. For example, the Velcro or snap example may be encapsulated in a material that prevents separation from its underlying member 13A or 13B. As another example, the bolt through the sleeve can be welded to the underling sleeve, undesirably preventing its removal. Those skilled in the art nevertheless may form the unmovable connectors in other ways, such as by welding the connector 26A or 26B directly to its member 13A or 13B, or some other permanent and unmovable connection mechanism.

Figure 11:
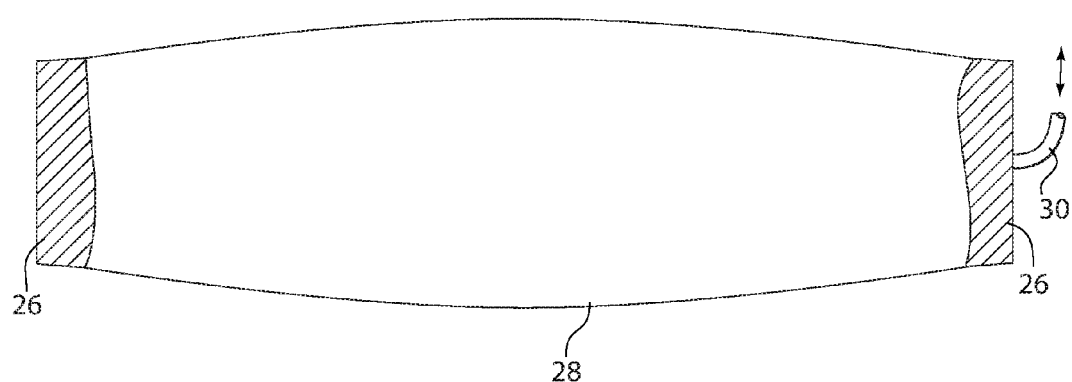
FIG. 11 schematically shows more details of a bundle of actuators in accordance with other embodiments of the invention.

Some embodiments of the invention also may have an optional substrate or base ("substrate 28") of some form supporting the bundle 12 of activation elements 10. Dashed lines in FIG. 10 schematically show the substrate 28. Although extending slightly beyond the boundary of the bundle 12 in the figure, the substrate 28 may be thinner and thus, contact less than the entire surface area of the bundle 12. In a manner similar to the securing elements 26, the substrate 28 should be flexible and strong. FIG. 11 shows one embodiment in which the substrate 28 completely covers the bundle 12 of activation elements 10.

The bundle 12 also includes some mechanism for actuating the activation elements 10. For example, FIGS. 10 and 11 schematically show a tube 30 for channeling fluid, such as a liquid, to and from the activation elements 10 from a fluid driving and control source (not shown).

Those skilled in the art can vary the placement of the connectors 26A and/or 26B on its bundle 12. For example, some embodiments may position one or both of the connectors 26A and 26B at the ends of the bundle 12, as shown in FIGS. 8A-11. Other embodiments, however, may position the connectors 26A and/or 26B somewhere between the ends of the bundle 12. In fact, some embodiments may have more than two connectors 26A and 26B.

The connectors 26A and 26B may be moved in any of a variety of different ways. For example, they may be manually movable by a user of the underlying device. Alternatively, the system may have logic and some movement mechanism, such as a stepper motor, to move one or both of the connectors 26A and 26B in response to some stimulus or condition.

Although the description above contains many specific examples, these should not be construed as limiting the scope of the embodiments of the present disclosure but as merely providing illustrations of some of the presently preferred embodiments of this disclosure. Thus, the scope of the embodiments of the disclosure should be determined by the appended claims and their legal equivalents, rather than by the examples given.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the embodiments of the present disclosure.

I claim:

1. A system, comprising:
   a first member;
   a second member;
   at least one artificial muscle style activation element configured to move the first member relative to the second member, wherein the activation element is configured as a hydraulic activation element; and
   a primary movable connector secured to the at least one artificial muscle style activation element, the primary movable connector being movable along the first member between at least a first location and a second location, and the primary movable connector selectively, releasably securing the at least one artificial muscle style activation element to the first member at the first location during a first mode and at the second location during a second mode;
   wherein the at least one artificial muscle style activation element is connected to the second member.

2. The apparatus as defined in claim 1, wherein the first member or the second member is a robotic arm that is separate from the artificial muscle style activation element.

3. The system of claim 1, wherein the first member is connected to the second member by a hinge joint.

4. The system of claim 1, further comprising a second movable connector secured to the at least one artificial muscle style activation element, the second movable connector being configured to move along the second member between at least a first location and a second location, and the primary movable connector being configured to selectively, releasably secure the at least one artificial muscle style activation element to the second member at the first location during a first mode and at the second location during a second mode.

5. The system of claim 1, wherein the at least one artificial muscle style activation element is fixedly connected to the second member.

6. The system of claim 1, wherein the primary movable connector comprises a slide carriage configured to slide along the first member, and wherein the primary movable connector further comprises a device operable to prevent sliding movement of the slide carriage when the device is in a first configuration and operable to enable sliding movement of the slide carriage when the device is in a second configuration.

7. A hydraulic system, comprising:
   a first member;
   a second member configured with the first member;
   a hydraulic artificial muscle style activation element configured to move the first member relative to the second member; and
   a movable connector secured to a first end of the activation element;
   wherein the movable connector moves between at least a first location on the first member and a second location on the first member;
   wherein the movable connector selectively, releasably secures the activation element to the first member at the first location during a first mode and at the second location during a second mode; and
   wherein a second end of the activation element is connected to the second member.

8. The apparatus of claim 7, wherein the primary movable connector comprises a securing device configured to
   secure the activation element to the member at the first connected location;
   release the activation element from the member such that the primary movable connector is operable to be moved between the first and the second connected locations; and secure the activation element to the member at the second connected location.

9. The apparatus of claim 8, wherein the securing device comprises a biased fastener.

10. The apparatus of claim 8, wherein the securing device is automatically actuated.

* * * * *